United States Patent [19]
Heule

[11] 3,980,075
[45] Sept. 14, 1976

[54] PHOTOELECTRIC PHYSIOLOGICAL MEASURING APPARATUS

[75] Inventor: James E. Heule, Minneapolis, Minn.

[73] Assignee: Audronics, Inc., Minneapolis, Minn.

[22] Filed: Sept. 27, 1974

[21] Appl. No.: 510,006

Related U.S. Application Data

[63] Continuation-in-part of Ser. No. 330,683, Feb. 8, 1973, abandoned.

[52] U.S. Cl. .................. 128/2.05 R; 128/2.05 P; 128/2.05 T; 128/2.05 V
[51] Int. Cl.² ........................................ A61B 5/02
[58] Field of Search ............... 128/2.05 R, 2.05 P, 128/2.05 V, 2.05 T, 2.05 E, 2.05 F, 2.05 N, 2.05 A, 2.06 R, 2 L; 356/39–41

[56] References Cited
UNITED STATES PATENTS

| | | | |
|---|---|---|---|
| 3,051,165 | 8/1962 | Kompelien | 128/2.05 A |
| 3,139,086 | 6/1964 | Botsch et al. | 128/2.05 P |
| 3,228,391 | 1/1966 | Fitter et al. | 128/2.05 T |
| 3,412,729 | 11/1968 | Smith, Jr. | 128/2.05 R |
| 3,575,162 | 4/1971 | Gaarder | 128/2.05 T |
| 3,628,525 | 12/1971 | Polanyi | 128/2.05 P |
| 3,638,640 | 2/1972 | Shaw | 128/2 L |
| 3,704,706 | 12/1972 | Herezfeld | 128/2.05 P |
| 3,776,221 | 12/1973 | McIntyre | 128/2.05 R |
| 3,796,213 | 3/1974 | Stephens | 128/2.05 R |
| 3,815,583 | 6/1974 | Scheldt | 128/2.05 P |
| 3,858,574 | 1/1975 | Page | 128/2.05 T |

FOREIGN PATENTS OR APPLICATIONS

| | | | |
|---|---|---|---|
| 1,962,335 | 3/1972 | Germany | 128/2.05 R |
| 1,186,123 | 4/1970 | United Kingdom | 128/2.05 P |
| 987,504 | 3/1965 | United Kingdom | 128/2.05 P |

OTHER PUBLICATIONS

Rentsch, "Thermistor Pulse Transducer", Med. and Biol. Eng., vol. 10, pp. 301–305, Permagon Press, 1972.

Cohen, "Led Skin Reflectance Oximeter", Med. and Biol. Eng., vol. 10, pp. 385–391, 1972.

*Primary Examiner*—Robert W. Michell
*Assistant Examiner*—Lee S. Cohen
*Attorney, Agent, or Firm*—Paul L. Sjoquist

[57] ABSTRACT

An apparatus is disclosed which comprises a photoelectric probe for introducing light pulses into a measurement area and for producing a measurement signal representative of the light as modulated in the measurement area, such modulation including modulations characteristic of the circulatory system blood volume variations of the area. Demodulation circuitry is disclosed which demodulates the meaningful from the non-meaningful data of the measurement signal, and utilization devices responsive to various characteristics of the meaningful data are disclosed, which utilization devices include a pulse wave meter, pulse amplitude meter, pulse rate meter, and tissue perfusion meter.

29 Claims, 9 Drawing Figures

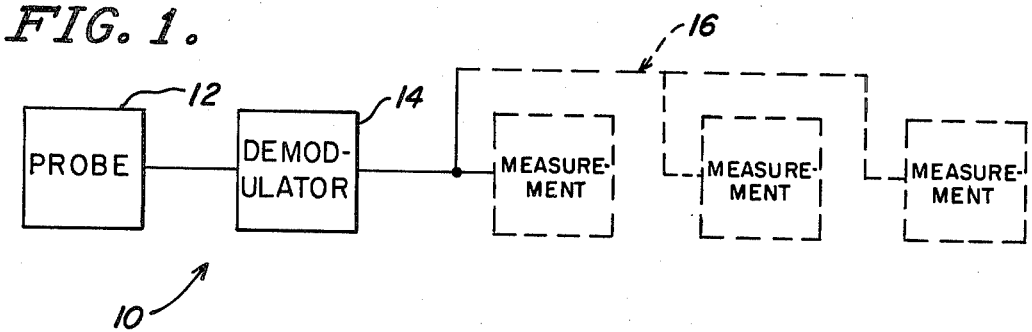
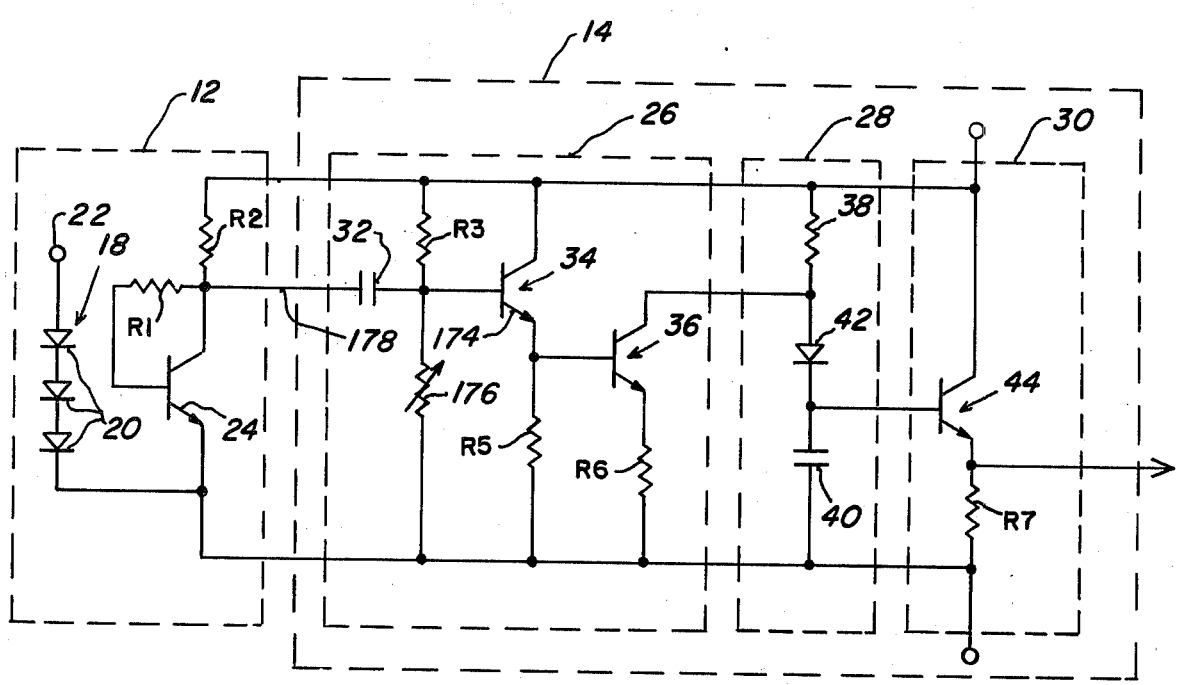
FIG. 2, Part A

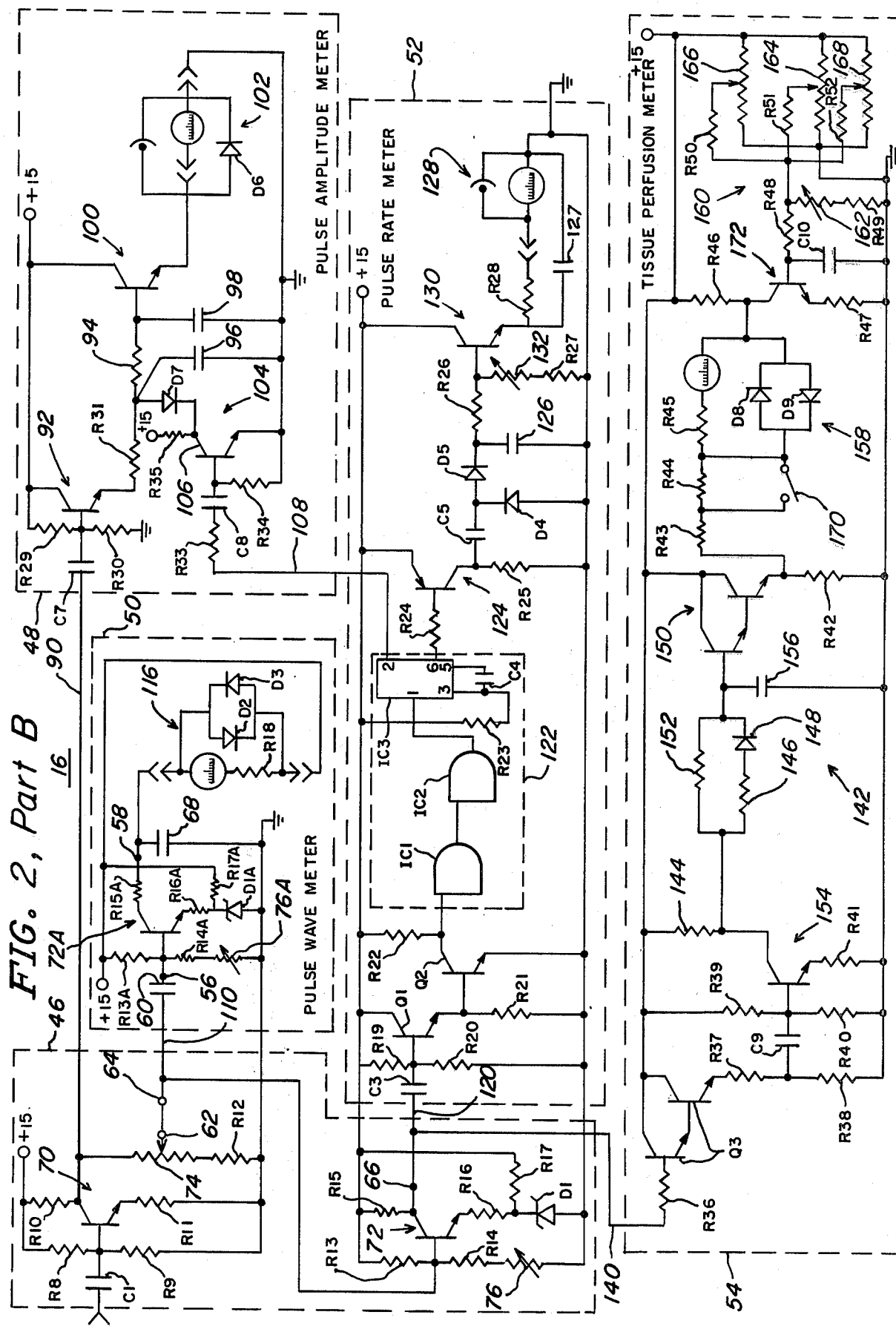
FIG. 2, Part B

FIG. 3.
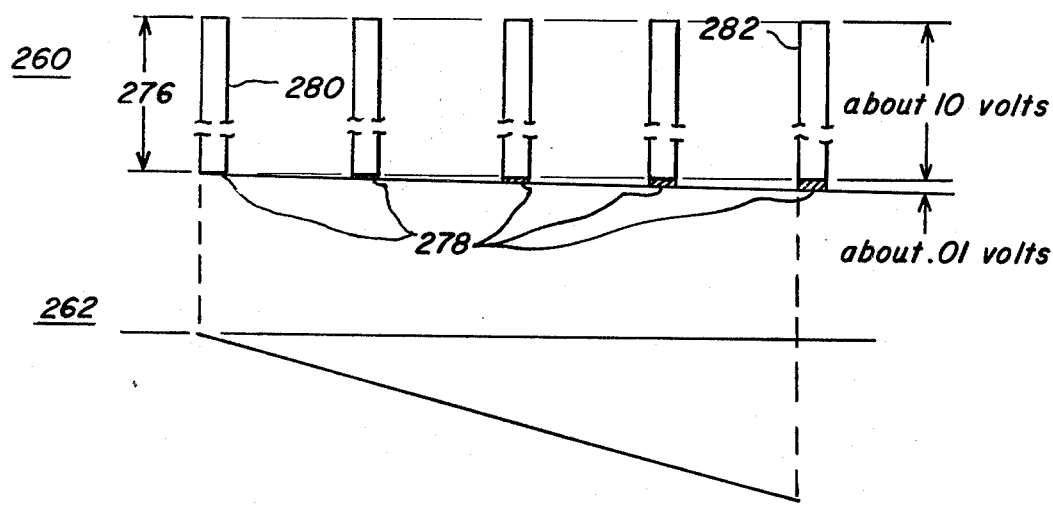
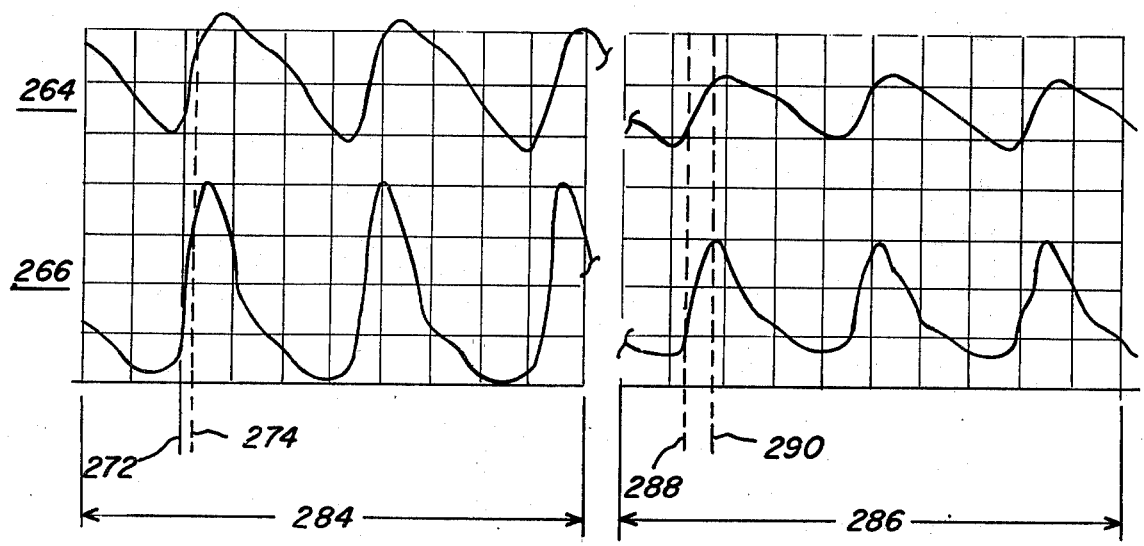

FIG. 5, Part A

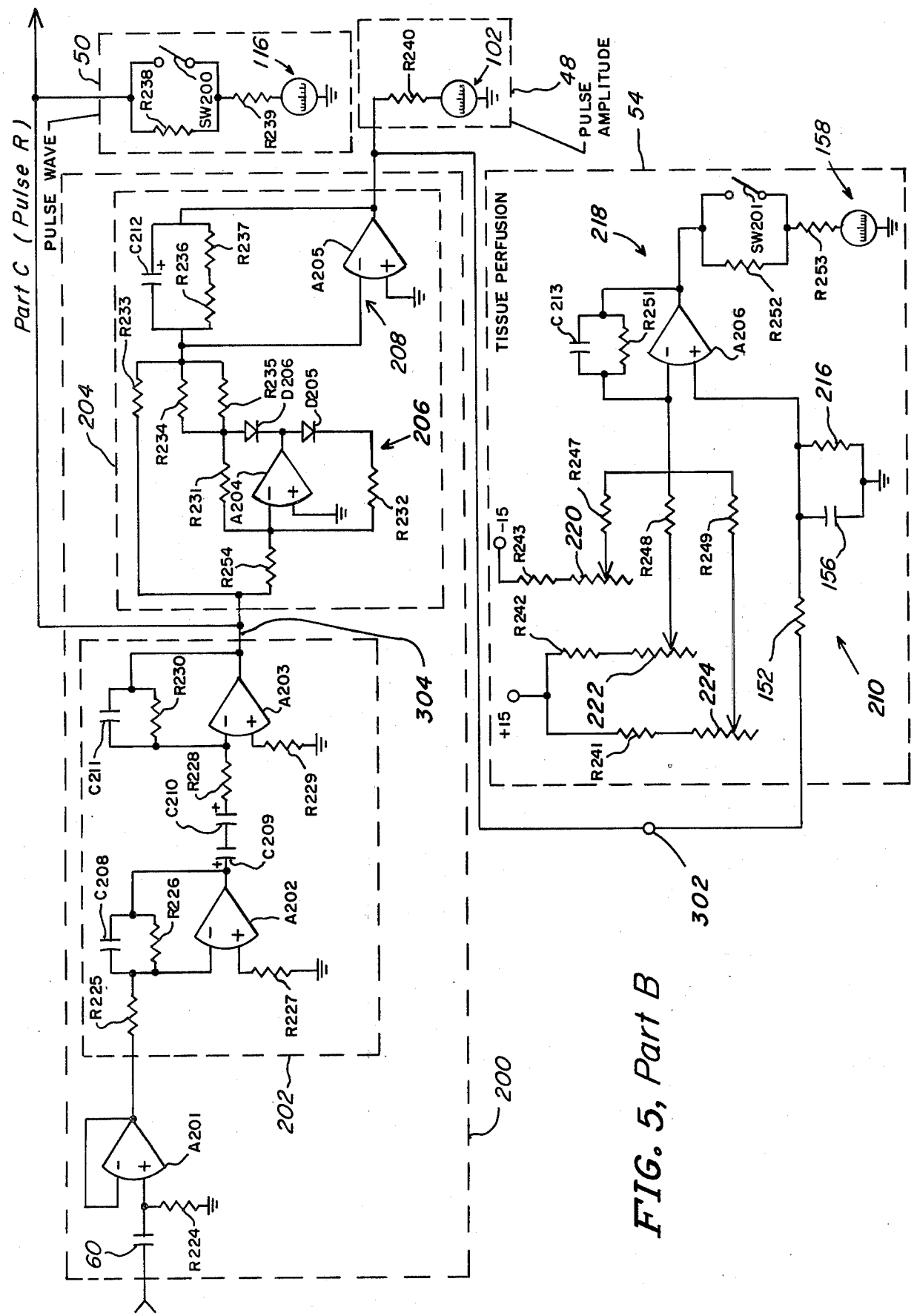
FIG. 5, Part B

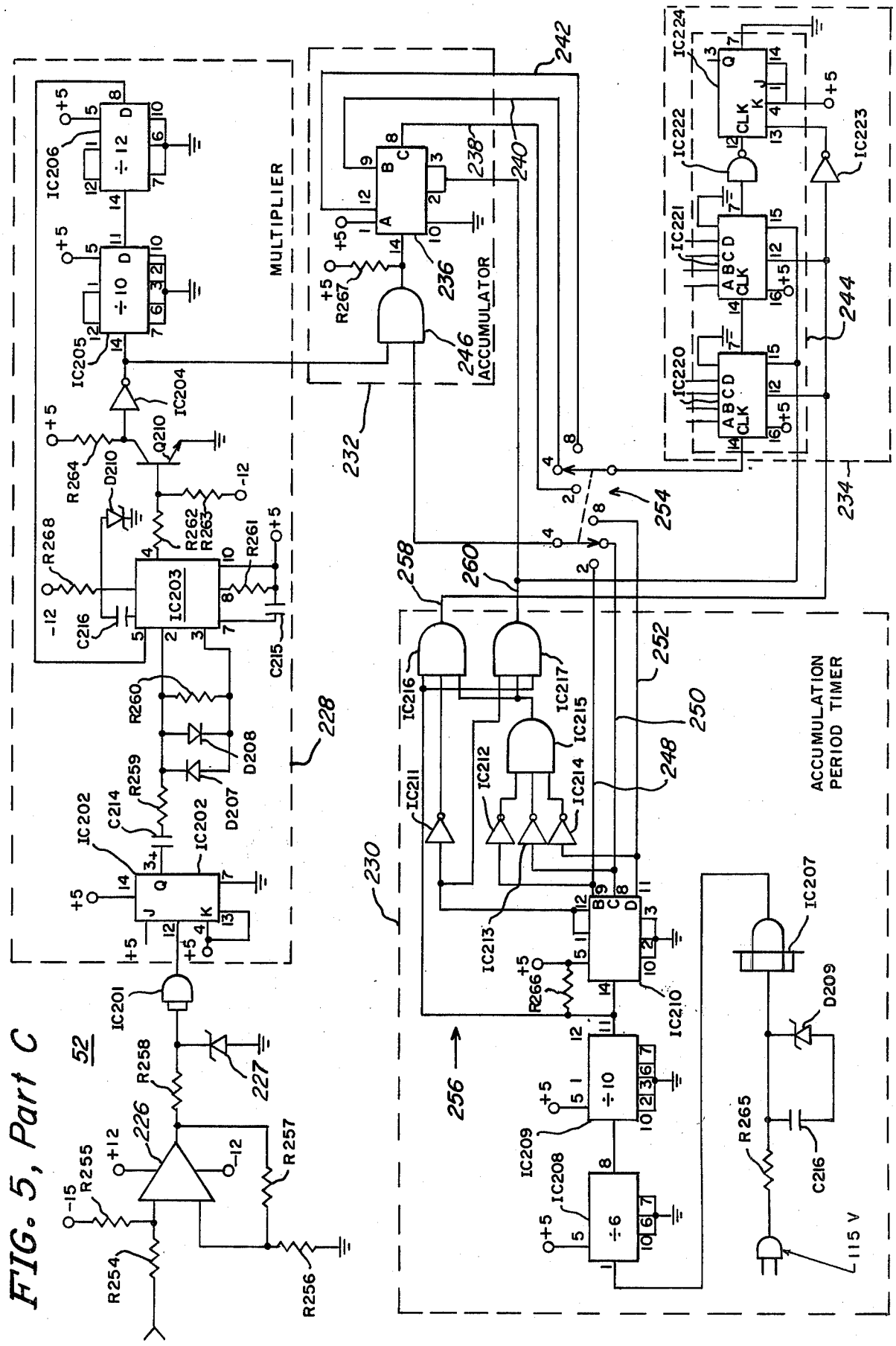
FIG. 5, Part C

PHOTOELECTRIC PHYSIOLOGICAL MEASURING APPARATUS

RELATED APPLICATIONS

This application is a continuation-in-part of U.S. patent application Ser. No. 330,683, filed Feb. 8, 1973, now abandoned, and assigned to the same assignee as the present invention.

BACKGROUND OF THE INVENTION

This invention relates to measurement of physiological data in general, in particular to measurement of data representative of the circulatory system, and specifically to photoelectric measurement of the blood volume waveform of the circulatory system. The circulatory system is contained in a continuous endothelial sac from the heart to the terminal microcirculation ending in the capillaries and venules. The covering of the endothelial sac varies from the thick muscular covering of the heart to no covering at all in the capillaries.

The control of the microcirculation, i.e., small arteries and veins, arterioles and meterarterioles, is essentially muscular and primarily neurogenic. The capillaries respond to local cellular needs, i.e., pH, $O_2$ levels and nutritional needs. The microcirculation functions to sustain life itself, the larger components of the system are merely subservient to local needs.

The function of blood pressure, i.e., heart action and compliance of larger vessels, are secondary to local needs of perfusion. These needs vary from second to second, from organ to organ; but the end result of all body functions is to maintain homeostasis of the total organism. As the organism ages or changes in response to any condition of stress or environment, drugs, disease, etc., the microcirculation makes compensatory corrections to meet these conditions of cellular demand. The microcirculation makes this change long before central reactions are noted in a compensatory way; indeed the central reactions are ultimately fixed in response to the continuing cellular demand of an aging or disease process. These same demands are evidenced in an acute way, i.e., shock, surgery or sudden environmental changes, usually well in advance of central changes.

By measuring changes in the microcirculation as they occur, it is possible to anticipate and correlate diagnosis and treatment of a great number of body conditions. Many ways have been devised to measure circulatory change; commonly used blood pressure cuffs, indwelling venous and arterial catheters, fiber optic catheters, angiography, dye dilution techniques, glass electrodes on muscle tissue, retinal microscopy, E.C.G., Doppler principle transducers, Wheatstone bridge plethysmography, microsurgery in animals, and many more. With few exceptions, most highly accurate techniques are invasive and are concerned mainly with the "large" circulation and its changes, changes brought about for the most part by demands of the microcirculation in response to life itself.

The present invention provides an apparatus for practicing a non-invasive, rapid technique for measuring microcirculatory homeostasis or change. It operates by the simple topical application of a probe on the skin, and includes circuitry which enables the user to "read" the microcirculation in any suitable area of the body.

DESCRIPTION OF THE PRIOR ART

The circulatory system characteristic of blood volume has long been recognized as an important element of diagnostic data. For example, the U.S. Pat. No. 161,821, which issued on Apr. 6, 1875, to E. A. Pond, is for a "Sphygmoscope." The Sphygmoscope is a forerunner of the apparatus which is now referred to as an oscillometer. Basically the sphygmoscope and oscillometer utilize the principle of hydraulics to measure blood volume. The earlier devices, such as the above referred to sphygmoscope, were essentially quantitative data measurement mechanisms in that they were mostly concerned with providing an indication of maximum and minimum blood volume. Later devices provided increasingly more sophisticated data as illustrated by U.S. Pat. No. 3,083,705 which issued Apr. 2, 1963, to Carl A. Johnson for Vascular Recording Apparatus. This patent discloses an oscillometric apparatus having a response time comparable to the electrocardiograph in that it records circulatory events occurring at intervals on the order of 0.04 seconds. In short, these later devices provide qualitative data, specifically data representative of the blood volume waveform, including such waveform characteristics as the crest time and time of the diastolic slope.

Improvements during the past 20 years, in part at least to overcome certain limitations of the hydraulic principle devices, have led to development of photoelectric measurement apparatus. While these photoelectric apparatus are free of certain shortcomings of the hydraulic devices, they are inferior in other respects. Specifically, the photoelectric devices of the prior art characteristically provide data of the end-point variety (systolic and diastolic pressures) together with other quantitative data such as pulse rate. These photoelectric devices provide measurements of physiological data by introducing light into a measurement area of the body. In the body, the light is modulated such as by absorption and reflection. The modulated light, after either transmission through or reemission from the body, is collected and demodulated. Generally, the circulatory system of the measurement area is the variable characteristic and the demodulated physiological data measured is thus representative of the circulatory system. Briefly, photoelectric devices provide a composite signal which includes both meaningful and non-meaningful data. Non-meaningful data includes data which is characteristic of the light source or electrical circuitry associated therewith, or data which is representative of circulatory system functions or structure not of direct and immediate interest in the test being performed. In separating (demodulating) the meaningful from the non-meaningful data, the devices distort the data such that, while still retaining quantitative data such as minimum and maximum pressures and pulse rate information the more sophisticated qualitative data of the blood volume waveform is "distorted," most often to the extent that no meaningful waveform qualitative data is provided.

One known photoelectric apparatus which provides a blood volume waveform of some utility, however, is disclosed in U.S. Pat. No. 3,412,729, which issued Nov. 26, 1968, to J. R. Smith, Jr. The apparatus of this Smith patent provides two representations of the blood volume waveform. A first representation is provided as the output of a DC amplifier (FIG. 1, element 50) which extracts the meaningful data by application of a "bucking voltage" which tends to cancel so-called direct current (DC) non-meaningful data. The bucking voltage is adjusted to a predetermined constant level. The DC non-meaningful data, however, is not a constant but varies according to such things as the physical position of the probe. Probe movement during a measurement has been found to be a problem, even when a patient has been anesthetized. The DC non-meaningful data, and hence the amount of bucking voltage which would be required, can also shift gradually in accordance with such factors as physiological changes in the patient which alter the optical properties of the tissues, including changes in fluid balance. These latter changes in particular can sometimes occur very rapidly and thus, from an electronic circuit standpoint, at the time of their occurrence they are effectively a high frequency signal which of course are not cancelled by the bucking voltage. As for the second waveform representation, it is provided as the output of a so-called AC amplifier (FIG. 1, element 60) and is useful for one of the objects of the patent, namely for determining the difference between systolic and diastolic pressures. This amplifier 60 provides a signal which is measured with reference to, and alternates between positive and negative excursions above and below, a potential of zero volts. For such an alternating signal, the peak positive excursion corresponds to systolic pressure and the peak negative excursion corresponds to diastolic pressure, the excursions are approximately equal, and an approximation of the pressure difference is simply either their difference or twice the positive peak excursion value. It is thus seen that according to Smith, a first waveform is provided which is subject to error as a result of changes in the non-meaningful data signal and a second waveform is provided which provides quantitative data.

SUMMARY OF THE INVENTION

The present invention is an electronic apparatus for continuously monitoring tissue perfusion. The apparatus utilizes a pulsed light source and sensor mounted in a probe, which is attached to the outer surface of the patient's skin by non-invasive techniques. The apparatus provides an indication of one or more body functions of interest to the physician treating the patient. In the preferred embodiment, the following four indications are provided by the electronic circuits connected to the sensor:

Pulse rate

The sensor signal is amplified, demodulated, filtered and processed through a suitable indicator circuit to provide a direct count indication of the patient's heart beat.

Pulse wave

The sensor signal is amplified, demodulated, and passed through an electronic gain and filter circuit to provide an indication of cardiac output, particularly ventricular ejection, as seen by the tissues.

Pulse amplitude

The pulse wave signal is integrated over a predetermined time interval to provide an indication of the magnitude of the excursion between minimum and maximum values of the pulse wave signal. The resultant signal provides an indication of the left ventricular capacity.

Vaso bed

The pulse amplitude signal is integrated over a predetermined time interval to provide an indication of the patient's average, or baseline, tissue perfusion. The continuing monitoring of tissue perfusion changes provides a predictive and diagnostic tool for impending shock, blood loss, cardiac failure, dilution effects, etc. This indication provides an early warning which can be used to evaluate the total body reaction to a given set of circumstances, both vasodilation and vasoconstriction.

Photoelectric measurements of the circulatory system provide a composite signal representative of all activity and structures in the measurement area. The blood volume waveform, including qualitative data free of distortion of high frequency non-meaningful data, is provided by extracting from said composite signal those variations having a frequency greater than about 10 Hz. Such a waveform permits measurement of qualitative data such as data of the left ventricular ejection phase of a heart beat cycle and also permits of accurate measurement of quantitative data such as tissue perfusion. According to a further feature of the invention non-meaningful low frequency data components are also removed from the composite signal.

In a preferred embodiment, extraction of meaningful data signals from high and low frequency non-meaningful data is accomplished by means of a combination shunt and series capacitor. The embodiment measures a reflected signal (as opposed to a signal transmitted entirely through a body member) and the embodiment also operates in a pulsed mode; the pulse duty cycle is about ten percent (approximately a 100 micro-second pulse interval and a 900 microsecond inter-pulse interval). The shunt capacitor is chosen to have a capacitive reactance at high frequencies (frequencies above about 10 Hz.) which is low to provide a shunt path to ground thereby extracting such high frequency signals from the composite signal. For this pulsed mode embodiment, the capacitor also performs an integrating function to further demodulate the composite signal. The non-relevant data of the composite signal includes a base component which is by far the largest of the components making up the composite signal. The signal base component includes light reflected from the various skin layers, tissue cells and other matter not a part of the circulatory system. The base component has been found to represent up to 99 percent of the composite signal, and includes the aforementioned DC component discussed with reference to the Smith patent. The capacitive reactance characteristic of the series capacitor effectively blocks the complete range of base component signal low frequency non-relevant data signals. In selecting the values of the components which make up the charge and discharge time constants of the circuit, for a pulsed mode operated embodiment, values are chosen which provide a charge time constant fast enough to preserve the waveform. For the preferred embodiment inter-pulse interval of 900 micro-seconds, relevant data signal peak amplitude of about 0.01 volts amplified and applied to the integration capacitor, and a ratio of relevant to non-relevant data of about 1 to 99, an integration circuit having a charge time constant of about 0.001 second and a discharge time constant of about 0.1 second provides an accurate waveform. (The terms "low" and "high" frequency are used in a relative sense and not in a literal technical sense of precise frequency ranges as set forth in manuals of electronic standards). Also, definition of the discharge time constant in terms of the amplitude of the relevant data signal is in terms of an assumed mean-value signal since the actual signal does of course vary in amplitude.

BRIEF DESCRIPTION OF DRAWINGS

FIG. 1 is a block diagram illustration of a photoelectric physiological data measuring system according to the present invention;

FIG. 2, Parts A and B, is an electrical schematic diagram of an essentially discrete component implementation of the system of FIG. 1;

FIG. 3 is an illustration of waveforms representative of a blood volume waveform at various points in the circuit of FIG. 2;

FIG. 5, Parts A, B and C, is a schematic diagram of a basically integrated circuit implementation of the system of FIG. 1; and, FIG. 6 is a block diagram of digital readout circuitry for use in combination with the measurement devices of FIG. 5.

DESCRIPTION OF THE PREFERRED EMBODIMENT

Figure 4:
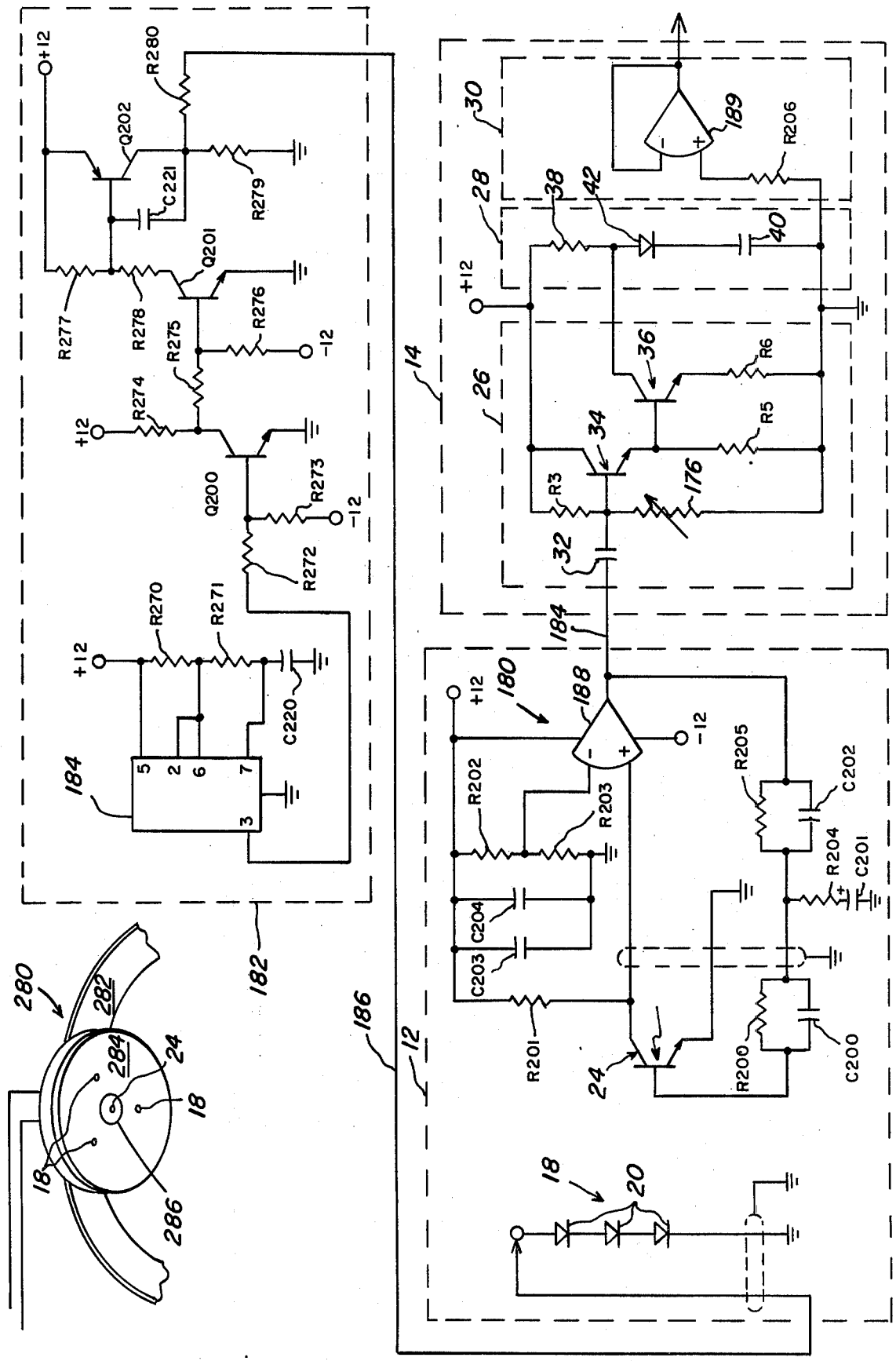
FIG. 4 is a mechanical schematic diagram of the probe 12 or FIG. 2.

Referring now to FIG. 1, a photoelectric physiological data measuring system is shown generally as 10. The system includes a photoelectric probe 12 and a demodulator circuit 14. Photoelectric probes are well known in the art, and include both those which measure relected light and those which measure light transmitted through the body. The demodulator 14 includes a circuit for operating on a composite signal from probe 12 to extract signal variations less than about 10 Hz. to provide a demodulated signal the waveform of which includes circulatory system qualitative data free of distortion by non-meaningful high frequency data. The exact method of extraction is immaterial; an amplifier or filter for preferentially passing the desired signal or a shunt or blocking circuit for selectively removing undesired signal may be used.

Also shown in FIG. 1 by means of phanton lines are a group of blood volume waveform measurement devices shown generally as 16. Such devices may be any of a variety of well known devices, such as a graphic recorder, also known as a strip or pen recorder, or a pulse rate meter. The devices may also be measurement apparatus such as tissue perfusion and left ventricular ejection meters.

FIG. 2 is a schematic diagram of a basically discrete component implementation of a preferred embodiment of a measurement system as shown in FIG. 1. As shown, probe 12 includes a light source, shown generally as 18, which consists of three light emitting diodes 20 adapted by a terminal 22 for interconnection to an energy source, not shown. Also included in probe 12 is a photo-transistor 24. The mechanical structure for mounting the diodes 20 and photo-transistor 24 is not shown as it may take any of a variety of configurations. U.S. Pat. Nos. 3,040,737 issued June 26, 1962 to A. D. Kompelien et al. and 3,602,213 issued Aug. 31, 1971 to William L. Howell and William B. Leaf disclose two such configurations. In the actual embodiment, the phototransistor 24 is mounted in the center of a flat circular disc. The three diodes are positioned on radials forming angles of 120° about midway between the center and outer periphery of the disc. The diodes 20 are optically isolated from phototransistor 24. More important than the mechanical structure of the probe 12, is the optical characteristics of the diodes 20. The exact diodes employed in the preferred embodiment are set forth in Table 1 hereinafter. The important optical characteristics of the diodes 20 are that they provide light at a wavelength other than that of ambient light (i.e., light from ordinary incandescent and fluorescent lamps) and at a wavelength insensitive to blood oxygen saturation of the blood. The diodes 20 of the preferred embodiment have a wavelength peak emission of 9,000 A. Such a wavelength also provides good penetration of the epidermis, dermis, and subcutaneous layers of the skin, and is minimally absorbed by the skin pigments B-carotene and melanin to permit use of low wattage diodes to avoid excessive tissue heating. When the diodes are operated in a pulsed mode, the diodes 20 can even be safely over-driven. For the preferred embodiment duty cycle of ten percent and pulse interval of one-hundred microseconds, each diode is driven by a current of 83.5 milli-amps which amounts to overdriving the diode steady state maximum rating by about 67%. This 83.5 milli-amp driving current is provided by a pair of monostable multivibrators (not shown), one for pulse duration and the other for repetition rate. Each multivibrator is a separate integrated circuit; both are externally adjustable, regeneratively connected by four gates and drive a high speed silicon transistor. In order to respond fast enough to a pulse and be sufficiently responsive at wavelengths about 9,000 A, a silicon phototransistor is employed as photodetector 24.

Referring again to FIG. 2, the demodulator circuit 14 is shown as comprising an input interface section 26, combination shunnt and integration section 28, and an output interface section 30. The input section 26 includes an isolation capacitor 32, an impedance matching emitter follower shown generally as 34 and a common emitter amplifier shown generally as 36. Demodulator 28 includes a resistor 38 and capacitor 40. Also included in demodulator 28 is a diode 42 which is necessary, in a pulsed mode operation embodiment such as that of FIG. 2, in order to prevent excessive discharge of capacitor 40 through common emitter amplifier 36 during inter-pulse intervals. The output stage 30 comprises another impedance matching emitter follower shown generally as 44. It is not essential that the demodulator 28 be intermediate the input and output sections 26 and 30. The demodulator could, for example, precede the input section 26 in which case a collector resistor would need to be provided for amplifier 36 because resistor 38 serves as both such a collector resistor and as the resistive component of an integrator formed principally by the resistor 38 and capacitor 40. In addition to being the capacitive component of the integrator, capacitor 40 is a shunt path for high frequency non-meaningful data signals.

The balance of FIG. 2 comprises a group of utilization devices shown generally as 16. This group of devices includes an input interface section shown generally as 46 and four meter sections. One meter section is a pulse amplitude meter, shown generally as 48, another a pulse wave meter, shown generally as 50, a third is a pulse rate meter, shown generally as 52, and the other meter section is a "vaso bed" or tissue perfusion meter, shown generally as 54. Briefly, the input interface section 46 provides impedance matching to the probe circuitry which derives a signal representative of the blood volume waveform from the composite measurement signal which corresponds to the light pulses as modulated in the measurement area. Section 46 also includes those stages of amplification common to two or more meter sections, in order to avoid redundant circuitry. A further consolidation of circuitry is possible and was actually made in the actual embodiment which corresponds to FIG. 2; specifically, it is possible to entirely eliminate the circuitry between nodes 56 and 58 in pulse wave meter 50 by reconnecting capacitor 60 at nodes 62 and 64 and interconnecting node 58 to node 66. The reason for including the redundant circuitry in FIG. 2 will be made apparent shortly.

Considering now the input interface section 46 of the utilization devices 16, it comprises merely a pair of common emitter amplifiers and their associated biasing components. The common emitter amplifier 70 in addition to providing signal amplification, provides impedance matching with and is capacitively coupled to the output interface section 30 of demodulator 14. Further amplification is provided by the second common emitter amplifier, shown generally as 72. Also included in interface section 46 are variable resistances 74 and 76.

The pulse amplitude meter 48 provides an indication of the waveform characteristic of pressure; specifically, meter 48 indicates the difference between the waveform maximum and minimum pressures (the systolic and diastolic pressures, respectively). Meter 48 amplifies the waveform signal provided by the input interface section 46 on lead 90 by means of amplifier 92. The waveform signal after amplification by amplifier 92 is integrated by the combination of resistor 94, capacitor 96, and capacitor 98 and applied to the base of amplifier 100 which drives a conventional D'arsonval pointer-indicator meter 102. Also included in pulse amplitude meter 48 is a compensation circuit, shown generally as 104, which compensates for variations in heart beat rate. Without such a compensation circuit, an increase in heart rate would appear on indicator 102 as an increase in the pressure differential between systolic and diastolic pressures and, conversely, a decrease would appear as a pressure differential decrease. Compensation circuit 104 provides, during a portion of each waveform pulsatile representation of a heart beat, essentially a short circuit to ground for both the pulse waveform representation out of amplifier 92 and the discharge path of the integrating components of resistor 94 and capacitors 96 and 98. The compensation circuit 104 provides this short circuit to ground for a fixed interval. As the heart beat rate increases, the short circuit exists a greater percentage of the time and, conversely, as the heart beat rate decreases, the short circuit exists a lesser percentage of the time. Briefly, compensation circuit 104 includes a transistor gate 106 conduction of which is controlled by impulses received via lead 108 from a monostable multivibrator (single-shot) of the pulse rate circuit 52.

The pulse wave meter 50 shown in FIG. 2 is specifically designed to preferentially measure signals of a frequency in the range of about 3.75 Hz. to 6.75 Hz. in the signal it receives on lead 110 from input interface section 46. For the actual embodiment of the preferred embodiment illustrated in FIG. 2, capacitors 60 and 68 were selected to have a value providing a frequency response curve the 3 db points of which are 0.63 Hz. and 40 Hz.; the curve is essentially flat within a range from 3.75 Hz. to 6.75 Hz. to preferentially amplify components of a waveform within this range. Series coupled capacitor 60 attenuates signals of a frequency below about 3.75 Hz. and shunt connected capacitor 68 shunts to ground signals above about 6.75 Hz. Briefly, the waveform components within this range are those representative of the heart beat phase known as "left ventricular ejection." It is sufficient for purposes of this discussion, that it be understood that the capacitors 60 and 68 emphasize the left ventricular ejection phase of the heart beat cycle. When the probe 12 is positioned over an arterial measurement area, the effect of capacitors 60 and 68 is to preferentially pass the left ventricular ejection phase of a heart beat waveform and attenuate other phases of the waveform, particularly those immediately preceding and succeeding the left ventricular phase. When the probe 12 is positioned over a microcirculatory area, the waveform represents blood flow at a significant distance from the heart and in vessels small compared to the arteries. The blood waveform loses some of the waveform arterial characteristics, including the steepness of the slope of the waveform leading edge of each heart beat pulse in traveling such a distance and as a result of the damping effect of the small vessels of the microcirculation. This leading edge corresponds to the left ventricular ejection phase of the heart beat cycle. When the probe 12 is positioned over a microcirculatory area, the effect of capacitors 60 and 68 is to restore the left ventricular ejection characteristic to the waveform thereby permitting a measurement of the microcirculation, typically used for indicating tissue perfusion, to also provide qualitative waveform data such as left ventricular ejection. Also included in pulse wave meter 50 is a common emitter amplifier 72A and a D'arsonval movement pointer indicator 116. As previously stated, the amplifier 72A is redundant and can be eliminated simply by re-positioning capacitor 60 and re-connecting node 58. The amplifier 72A was included in FIG. 2 in order to permit a logical grouping of the various circuit components into input interface section 46 and four meter sections 48, 50, 52 and 54.

The pulse rate meter 52 derives its input from the second amplifier 72 of the input interface section 46 via lead 120. Basically, the meter 52 counts the pulsatile waveform representations of heart beats, each pulsatile representation ("pulse") corresponding to a single heart beat. According to the illustrated embodiment, each pulse is converted to a unit of voltage and applied to a voltage integrator. Accordingly, the voltage stored by the voltage integrator at any time is representative of pulse rate. Meter 52 includes a monostable multivibrator (single-shot) circuit shown generally as 122. Each pulse received on lead 120 triggers the multivibrator 122 into its unstable state. For the illustrated embodiment constructed using components as set forth in Table 1 hereinafter, the unstable state period is 153 milliseconds. One output of multivibrator 122 is the lead 108 which previously was said to provide a signal for controlling the transistor gate 106 of compensation circuit 104 and thus the compensation circuit 104 of meter 48 is operative to discharge integration capacitors 96 and 98 for a period of 153 milliseconds of each heart beat pulse. Another output of multivibrator 122 is amplified by common emitter amplifier 124 and applied to meter 52 integrating capacitors 126 and 127. The voltage stored in these capacitors at any time is proportional to the pulse rate. The capacitor 126 stored voltage is applied to an indicating meter 128 by amplifier 130 to provide an indication of pulse rate.

The vaso-bed or tissue perfusion meter 54 likewise takes its input from section 46 amplifier 72 but by means of lead 140. Meter 54 functions to average pulsatile waveform representations over a predetermined period, to provide an averaged signal representative of tissue perfusion. The illustrated preferred embodiment, constructed using components as set forth in Table 1, makes it possible to determine the overall general health, and to diagnose certain specific diseases, disorders and conditions of a patient based on the degree of and characteristic changes of tissue perfusion. Briefly, the tissue perfusion meter 54 consists of an integrating circuit shown generally as 142. The charging path for integrating circuit 142 includes resistors 144 and 146 and diode 148. The discharge paths include Darlington amplifier 150 and resistor 152 through amplifier 154. The time constant of the discharge path is about 50.0 seconds in order to store a charge in capacitor 156 representative of about 60 heart beats of a normal, healthy adult. Darlington amplifier 150 is employed to insure an input impedance to capacitor 156 sufficiently high to maintain a high enough ratio of discharge to charge time constants. Other components, e.g., a field effect transistor, would of course also provide a sufficiently high input impedance. The readout portion of tissue perfusion meter 54 includes a D'arsonval movement pointer indicator 158 and a meter calibrating and nulling section shown generally as 160. Variable resistor 162 is for calibration as described hereinafter; variable resistors 164, 166 and 168 are for nulling pointer indicator 158. A switch 170 provides precise nulling of pointer indicator 158.

The foregoing description of FIG. 2 sets forth the principal components and describes the important characteristics thereof of the probe 12, demodulator 14 and utilization devices 16. The component descriptions of these and the balance of the components of the preferred embodiment of FIG. 2 are set forth in Table 1 below:

TABLE I

Probe 12
R1 = 4.7 × 10$^6$ ohms
R2 = 1 × 10$^3$ ohms
20 = Monsanto, ME60 Light Emitting Diode
24 = Fairchild, FPF 130, Photo-Transistor
Probe housing (no reference No.) electrically insulative material; can be fabricated from a 1.2 in. outside diameter slug of delrin or bakelite 1.12 in. dia. by .983 in. deep bore

Demodulator 14
R3 = 300 × 10$^3$ ohms
176 = 10$^{200}$ × 10$^3$ ohms, trimpot, Spectrol 41;
R5 = 1 × 10$^3$ ohms    32 = 0.01 micro-farads
R6 = 270 ohms    40 = 0.1 micro-farads
R7 = 47 × 10$^3$ ohms    42 = 1N4154 diode
38 = 10 × 10$^3$ ohms    34, 36 and 44 = 2N 3392, NPN transistor

Utilization Devices 16
Input Interface 46
R8 = 56 × 10$^3$ ohms    D1 = Zener Diode, 1N5229
R9 = 8.2 × 10$^3$ ohms    C1 = 50 micro-farad, electrolytic
R10 = 2.2 × 10$^3$ ohms    70 & 72 = 2N3392, NPN transistors
R11 = 220 ohms
R12 = 12 × 10$^3$ ohms
R13 = 430 × 10$^3$ ohms
R14 = 270 × 10$^3$ ohms
R15 = 43 × 10$^3$ ohms
R16 = 3.0 × 10$^3$ ohms
R17 = 560 ohms
74 = 10 × 10$^3$ ohms trimpot; Spectrol 41
76 = 100 × 10$^3$ ohms trimpot; Spectrol 41

Pulse Wave 50
13A = 430 × 10$^3$ ohms    60 = 1.0 microfarad
R14A = 270 × 10$^3$ ohms    68 = .01 microfarad
R15A = 43 × 10$^3$ ohms    D1A = 1N5229, Zener Diode
R16A = 3.0 × 10$^3$ ohms    D2 = 1N4154 diode
R17A = 560 ohms    D3 = 1N4154 diode
R18 = 1 × 10$^3$ ohms    72A = 2N3392, NPN, transistor
76A = 100 × 10$^3$ ohms trimpot; 116 = 0–200 micro. amp., edgewise,

TABLE I-continued

Spectrol 41    D'arsonval movement meter; Honeywell MCE 1

Pulse Rate 52
R19 = 820 × 10$^3$ ohms    C3 = 2.0 microfarad; electrolytic
R20 = 100 × 10$^3$ ohms    C4 = 3.9 microfarad; tantalum
R21 = 10 × 10$^3$ ohms    C5 = 6.0 microfarad; electrolytic
R22 = 10 × 10$^3$ ohms    C6 = 1 × 10$^3$ microfarad; electrolytic
R23 = 56 × 10$^3$ ohms    126 = 100 microfarad; electrolytic
R24 = 470 ohms    D4 = 1N4154 diode
R25 = 3.0 × 10$^3$ ohms    D5 = 1N4154 diode
R26 = 4.7 × 10$^3$ ohms    128 = 0–00 micro. amp., edgewise,
R27 = 3.0 × 10$^3$ ohms    D'arsonval movement, meter;
R28 = 10 × 10$^3$ ohms    Honeywell MCE-1
132 = 10 × 10$^3$ ohms trimpot; 130, Q1 & Q2 = 2N3392, NPN transistor
Spectral 41    124 = 2N3905, PNP, transistor
IC1 & IC2 = NAND gate, integrated circuit type MC672
IC3 = toggle flip-flop, integrated circuit type MC667

Pulse Amplitude 48
R29 = 47 × 10$^3$ ohms    96 = 50 microfarad; electrolytic;
R30 = 3.3 × 10$^3$ ohms    98 = 25 microfarad; electrolytic;
R31 = 330 ohms    C7 = 25 microfarads, electrolytic;
    C8 = .47 microfarads
R33 = 1 × 10$^3$ ohms    D6 & D7 = 1N38A diode
R34 = 100 × 10$^3$ ohms    92, 100 & 106 = 2N3392, NPN,
R264    transistor
R35 = 4.7 × 10$^3$ ohms    102 = 0–200 micro-amp, edgewise,
94 = 100 ×Divide 10$^3$    D'arsonval movement meter;
ohms
    Honeywell MCE 1

Tissue Perfusion 54
R36 = 100 × 10$^3$ ohms    Q3 & 150 = Darlington amplifiers,
R37 = 2.7 × 10$^3$ ohms    148, D8 & D9 = 1N4154 diodes
R38 = 2.7 × 10$^3$ ohms    154 & 172 = 2N3392, NPN transistors
R39 = 15 × 10$^3$ ohms    C9 = 50 microfarad; electrolytic
R40 = 2.7 × 10$^3$ ohms    C10 = 6 microfarad; electrolytic
R41 = 100 ohms    156 = 500 microfarad; electrolytic
R42 = 1 × 10$^3$ ohms    158 = 50-0-50 micro-amp, edgewise,
R43 = 18 × 10$^3$ ohms    D'arsonval movement meter;
R44 = 27 × 10$^3$ ohms    Honeywell MCE 1
R45 = 3 × 10$^3$ ohms    170-switch, momentary action;
R46 = 10 × 10$^3$ ohms    push button; SPST
R47 = 47 ohms
R48 = 56 × 10$^3$ ohms
R49 = 1 × 10$^3$ ohms
R50 = 39 × 10$^3$ ohms
R51 = 39 × 10$^3$ ohms
R52 = 39 × 10$^3$ ohms
144 = 1 × 10$^3$ ohms
146 = 3 × 10$^3$ ohms
152 = 100 × 10$^3$ ohms
162 = 1 × 10$^3$ ohms, trimpot, Spectrol 41
164, 166, 168 = 5 × 10$^3$ ohms, trimpot, precision, 10 turn, Duncan Pixie Having described how to make a specific preferred embodiment of the invention, and having discussed the general considerations and teachings which enable one of ordinary skill in the art to modify and construct equivalent embodiments of the invention as illustrated in and described with reference to FIG. 2, use of the embodiment of FIG. 2 shall now be described. Prior to its use, the physiological data measuring system 10 is calibrated. With the system energized calibration of demodulator 14 is as follows: a calibrated oscilloscope is connected to the emitter lead 174 of amplifier 34; probe 12 is attached or held on a strongly perfused area of a compliant peripheral circulatory system (for example, on the center of the soft pad on the underside of the thumb): variable resistor 176 is adjusted so that the peak of the negative going pulse displayed on the scope is 0.6 volt positive with respect to ground at maximum reflected signal level; the pulse amplitude meter reading should now be at least 200, if less than 200, the above procedure is repeated until a reading of at least 200 is obtained after, either, changing the probe site or placing the probe on another person. For the balance of the calibration, the probe 12 is positioned to receive none of its own reflected light, and no ambient light of varying intensity. Variable resistor 76 is adjusted to provide a current of 100 microamperes through pointer indicator meter 116, to thereby center the meter (the meter 116 has a 200 unit swing, each unit corresponding to 1 micro-ampere of current). A test signal from a 5-volt DC source in series with a sine wave generator set to provide a 600 millivolt peak to peak sine wave at a frequency of from 50 to 200 Hz. is introduced at the input to input interface section 46 (FIG. 2, Part B). Variable resistor 74 is then adjusted until a pointer movement of pointer indicator 116 from minus 50 to plus 50 results. With variable resistors 74 and 76 properly set, and again with no input signal to probe 12 other than ambient light, the tissue perfusion meter is calibrated. Variable nulling resistors 166 and 168 are set to zero dial readings. Zero adjust resistor 164 is set to provide a reading of 0.87 on its dial. Calibration resistor 162 is then set to provide a voltage of 0.7 volts at the collector of amplifier 172. To verify calibration, a test signal is introduced at the input of demodulator 14 on lead 178 which provides a low pointer indication of 10 and a high indication of 190 on the pulse wave meter indicator 116. These high and low indications should produce an indication on tissue perfusion meter 54 which, when nulled by means of the zero adjust calibration resistor 164, results in a zero adjust dial reading of 8.9. (The zero adjust dial readings of 0.87 and 8.9 respectively correspond to resistances of 435 and 4450 ohms.) The pulse rate meter 52 is calibrated by means of variable resistor 132. A test signal of known repetition is provided, such as optically at the probe or electronically at some other point in the circuit in advance of meter section 52. Variable resistor 132 is adjusted until meter 128 indicates a rate equal to the known repetition rate. Recommended repetition rates are: 50, 100, and 150 pulses per minute. With the system 10 properly calibrated, probe 12 is positioned over a measurement area. The probe 12 may be provided with a mounting strap such as is shown in one or more of the above referred to prior art patents, may be hand-positioned, or may be secured with adhesive tape, or any other suitable means so long as the probe 12 is secured free of movement and desirably secured so as not to affect the circulation such as by compression of circulatory vessels. Selection of the measurement area depends upon the data desired. Measurements such as tissue perfusion and left ventricular ejection are enhanced by astute selection of the measurement area. For example, the lower one-third of the leg over the tibia is a good microcirculatory measurement area in terms of providing a signal in which the microcirculatory vessels (as compared with general circulatory vessels) are favorably great as the source of the measurement signal, although the total signal strength will be weak. Such data would be indicated primarily by the tissue perfusion meter 54. By contrast, if data representative of the general circulation for measurement of left ventricular ejection is desired (this data is indicated by the pulse wave meter 50), the thumb or big toe is a good measurement area. From the standpoint of total signal strength, any highly vascularized area is suitable, the forehead being such an area. It is to be understood, however, that the system 10 will provide a measurement of left ventricular ejection even when probe 12 is positioned on the forehead and a measurement of tissue perfusion even when the probe 12 is positioned over an artery. This capability of multiple measurements from data of a single measurement area, particularly when displayed on indicators grouped on the face of a single instrument such as the instrument of system 10, permits a diagnostician to simultaneously view different but interrelated indications. So displayed, a diagnostician may synthesize the individual measurements to form diagnoses not possible from the measurements individually. It will also be appreciated that the multiple measurement capability from a single probe encumbers only a small area of a patient, a matter of relatively little importance where measurement is part of a routine physical examination in a doctor's office but of great importance when measurement is made during a surgical operation.

With the light source 18, and the balance of the circuitry of system 10 energized, pulses of light from source 18 having a duration of 100 micro-seconds, produced at a rate of one-thousand Hz., and of about 935 micro-watts each are introduced into a measurement area. Phototransistor 24 receives reflections of the pulses and provides a signal representative of the reflected pulses to demodulator 14. As previously stated, demodulator 14 integrates-out the low-frequency base component and extracts the high-frequency non-meaningful data to provide a demodulated signal of meaningful pulse waveform data to the utilization devices 16. As also previously stated, in the actual embodiment, distortion is introduced into the waveform in the input interface section 46 in order to emphasize the left ventricular ejection phase of the waveform by means of capacitor 60, or to restore the left ventricular ejection characteristic in the case of a measurement of a microcirculatory area. In the actual embodiment, this emphasized waveform is displayed by the pointer indicator 116. From experience, for a measurement taken from the forehead, a normal, healthy adult will produce a swing of indicator 116 of from a minimum of about 50 to a maximum of about 140 to 145. With the waveform emphasized by capacitor 60, certain characteristics of the left ventricular ejection phase of the heart beat are ascertainable from the nature of movement of pointer indicator 116. For example, a very rapid upward swing indicates a strong, rapid, ejection. Conversely, a slow upward swing, indicates a slow ejection phase. Indications of indicator 116 are also obviously of utility on a comparative basis to show a change in the nature of the left ventricular ejection. As previously pointed out indicator 116 is not limited to a pointer indicator, but can be of any numerous forms, including a waveform trace such as an oscilloscope display or strip recorder should an application require a less subtle representation of the waveform. The emphasized waveform is also provided by input interface section 46 to the pulse rate meter 52, and tissue perfusion meter 54. It will, therefore, be appreciated that the indications given by the tissue perfusion meter 54 are based on data of a distorted pulse waveform. Such distortion is of no consequence to this particular preferred embodiment. For the preferred embodiment, it has been empirically determined that an average patient (an adult in good health) will have a tissue perfusion reading of from 3 to 6, i.e., a reading which requires setting the zero adjustment nulling resistor 164 to a reading of from 3 to 6 in order to null the tissue perfusion meter. In order to obtain a precise null, switch 170 is actuated. Switch 170 is actuated only during the nulling procedure. A reading of from 3 to 6 corresponds to a resistance of resistor 164 of from 1500 to 3000 ohms. The pulse amplitude meter operates on an undistorted waveform received from input interface section 46 on lead 90. The meter 48 provides an indication of the peak to peak amplitude of the waveform, i.e., it measures the swing of the pulse wave meter 50. By proper selection of the gain (beta) of the transistor of amplifier 100 in meter 148, the swing measured by meter 48 corresponds to the swing of the indicator 116 of meter 50, such selection being a matter of trial and error. In other words if the swing of meter 50 for an applied signal is from 50 to 150, the transistor of amplifier 100 is selected to provide a reading of indicator 102 of 100. The pulse rate meter 52 merely converts each pulse to a unit of voltage by means of the single-shot 122 and integrates the unit voltage by means of a capacitor 126 to provide an analog representation of the pulse rate which is then (digitally) indicated by indicator 128. It can thus be seen, that use of the physiological data measuring system 10 is limited only by the background, qualifications, and perceptiveness of the interpreter of the measured data.

Referring now to FIG. 3, the operation of various circuits of the embodiment of FIG. 2 is illustrated by a series of waveforms shown as 260, 262, 264 and 266. Waveform 260 corresponds to a composite signal and waveform 262 corresponds to a signal having the low-frequency and high-frequency non-meaningful data removed. Waveforms 264 and 266 are actual oscilloscope traces of waveforms of unemphasized and emphasized waveforms, respectively. Waveform 264 was taken from the collector of amplifier 70 and waveform 266 was taken from node 58. The waveforms 260 and 262 represent the period of time illustrated on waveforms 264 and 266 as 272 to 274, a period of approximately 0.05 second. Waveforms 260 and 262 include only about every tenth pulse, the other pulses having been omitted for the sake of clarity. Briefly, waveform 260 illustrates a waveform having a nearly constant non-meaningful data signal component 276 of about ten volts and a meaningful data component 278 which varies from about zero volts for pulse 280 to about 10 millivolts for pulse 282. Waveform 262 is waveform 260 following amplitude reduction by amplifier 34, inversion and amplification by amplifier 36, and after integration-out of the base-component by capacitor 40 and amplification and inversion by amplifier 44. Waveforms 264 and 266 have two periods shown as periods 284 and 286. Period 284 is the waveforms resulting following moderate exercise and period 286 is a waveform taken during work activity involving no physical strain or exertion but including body movements typical of a person moving about in a work position while rested in a chair or on a work stand. The period 284 waveform shows a pulse rate of about 85 beats per minute, pulse amplitude of 8, and a slope of 4/0.25 or 16 as compared with a pulse rate of about 100 beats per minute pulse amplitude of about 5.0, and a left ventricular ejection having a slope (the slope from points 288 to 290) of about 2/0.55 or 3.6, for period 286.

In FIG. 4, a mechanical schematic diagram of a housing 480 for light emitting diodes 18 and a phototransistor 24 is shown. The housing 480 may be made of plastic such as Delrin (TM), Bakelite (TM), or any other convenient material. Attached to the front side of housing 480, is a clear plastic covering 484. Phototransistor 24 is mounted near the center of housing 480, beneath cover 484. Also mounted in housing 480, and spaced symmetrically are three light emitting diodes 18. In use, housing 480 is placed adjacent an area of skin from which a measurement is to be made by means of attachment 482. As explained elsewhere herein, the forehead is a preferred location for microcirculatory measurement. As also explained herein, any means may be used to secure a light source and its associated photodefector to a measurement area, so long as they are secured against movement in a manner which, for microcirculatory measurements, does not compress the measurement area. Also included in housing 480 intermediate light emitting diodes 18 and phototransistor 24 is a light baffle 486 which optically isolates phototransistor 24 from light emitting diodes 18.

Another embodiment of the system 10 is shown in FIG. 5. The system of FIG. 5 operates in substantially the same way as that of FIG. 2 to provide the same result. That is, the system of FIG. 5 introduces pulses of light into a measurement area, receives reflections of the pulses, and produces a pulse waveform signal representation of the reflections of the pulses. The system operates on the signal representation to provide indications of peak to peak waveform amplitude, to provide emphasis of the pulse waveform to emphasize the left ventricular ejection phase of the heart beat cycle, and to provide indications of pulse rate and tissue perfusion. FIG. 5, in addition to illustrating an embodiment employing integrated circuits, also illustrates variations in the form and arrangement of the electronic circuits by which the ultimate results of the present invention are accomplished. For example, in FIG. 2, the demodulator 14 was shown to include an input amplifier or impedance matching emitter follower 34, while by contrast in FIG. 5, the first stage of amplification is shown as included in probe 12. The reason for so arranging FIG. 5 relates to the functional relationship between the probe 12, phototransistor 24 and the first stage amplifier, specifically, in the FIG. 5 circuit the amplifier and phototransistor 24 are both included in the same electronic feedback loop and thus, although their individual primary functions are logically independent, and although their physical locations may differ, the electronic performance of their individual functions is interrelated such that it is considered preferable to group them as a unit for purposes of illustration and description of the electronic circuit.

Referring now to FIG. 5, Part A, a data measuring system includes a probe 12, a light source 18, phototransistor 24, a first stage of amplification shown generally as 180, a probe drive circuit 182, and a demodulator circuit 14. The system also includes a plurality of measurement devices which are shown in FIG. 5, Parts B and C. The first stage of amplifacation 180 amplifies the signal provided by phototransistor 24 and provides impedance matching between phototransistor 24 and demodulator 14.

As shown, the amplification stage 180 and phototransistor 24 are each interconnected as elements of a current feedback loop. Briefly, by so interconnecting phototransistor 24 and amplification stage 180, a change in the reference voltage applied to the inverting input of operational amplifier 188 is compensated for by a corresponding change produced by the feedback loop. Consequently, changes in the reference voltage are compensated for to avoid introduction of errors corresponding to such reference voltage changes. Briefly, the probe drive circuit 182 consists of a free-running multivibrator 184 which has a running rate of 1.2 kilo-hertz to provide a signal which after amplification and inversion is provided as a 1.2 kilo-hertz pulse modulated output on lead 186, each pulse of said 1.2 kilo-hertz output consisting of one each, equal duration, positive and negative going phase. The 1.2 kilo-hertz output is applied by lead 186 to the series coupled light emitting diodes 20 of a light source 18. Demodulator 14 is identical to the correspondingly numbered demodulator of the embodiment described with reference to FIG. 2 except for output interface section 30. The output interface section 30 of the embodiment of FIG. 5 employs a unity gain operational amplifier 189 which provides impedance matching between the balance of the demodulator 14 circuitry and the measurement devices 16.

The utilization devices 16 of FIG. 1, shown in Parts B and C of FIG. 5, illustrate that certain circuits perform dual functions. For example, the devices 16 include an input interface section 200 which includes circuitry which performs functions common to two or more of the four meter sections, the utilization devices 16 again including a pulse amplitude meter 48, pulse wave meter 50, pulse rate meter 52 (Part C), and tissue perfusion meter 54. The emphasis function associated with the pulse wave meter 50 is performed, as it is in the actual circuit corresponding to the embodiment of FIG. 2 in the input interface section of the utilization device 16. The equivalent of capacitor 68 of FIG. 2 is likewise provided in input interface section 200 by the two stages of a gain and filter network shown generally as 202, each of which stages consists of a negative feedback amplifier. Unlike its counterpart of the preceding embodiment of FIG. 2, the input interface section 200 of the present embodiment also includes the peak to peak waveform pulse amplitude derivation functions and a full wave rectification function which also is in effect an integration having a charge time constant of one and one-half seconds. The combined rectification-integration circuit is shown generally as 204. The output of rectification-integration circuit 204 is applied to both the pulse amplitude meter section 48 and the tissue perfusion meter section 54.

For the embodiment of FIG. 5, the pulse amplitude meter 48 and pulse wave meter 50 sections comprise merely indicators 102 and 116, associated current limiting resistors, and, in pulse wave meter section 50, a switch for increasing the meter sensitivity by short circulating one of the current limiting resistors. Because of the dual functional roles of the pulse amplitude circuitry, shown generally as consisting of a full-wave rectifier 206 and a negative feedback amplifier 208, the circuitry is included in the input interface section 200.

The tissue perfusion meter 54 is shown to comprise an integrator shown generally as 210, the charge time constant of which is essentially defined by resistor 152 and capacitor 156 and the discharge time constant of which is primarily capacitor 156 and resistor 216. Also included in tissue perfusion meter 54 is a negative feedback operational amplifier 218 and negative nulling, zero adjust, and positive nulling variable resistors shown respectively as 220, 222, and 224.

The pulse rate meter 52 (FIG. 5, Part C) is shown to comprise a level detecting amplifier 226 not unlike a Schmidt trigger which is responsive to about the midpoint amplitude of a heart beat pulse leading edge to saturate in one direction and to the midpoint amplitude of a heart beat pulse trailing edge to saturate in the other direction, thus squaring up and narrowing each heart beat pulse. Further wave shaping is provided by a zener diode 227. Also included in the pulse rate counter is a multiplying circuit 228, an accumulation period timer 230, an accumulator 232, and a digital display, shown generally as 234. Briefly, the frequency multiplying circuit 228 multiplies the actual heart beat rate by a factor of 60. This permits accumulating a count of the number of pulses for integral periods of seconds, dividing the accumulated count by the period to provide a dividend equal to the number of beats per minute, and strobing this number to the display section each period. The accumulator timer 230 determines the length of the counting period. For the illustrated embodiment, the period may be 2, 4 or 8 seconds, the longer the period, the greater the averaging out of momentary variations. Included in the accumulator 232 is an accumulator count division chip 236 having three outputs identified as 238, 240, and 242. Each output is active for a series of consecutive counts of 2, 4, and 8, respectively, and is selectively interconnectable to the input of the accumulator count register 244 of the digital display 234. The division chip 236 input is the output of an AND 246 the dual inputs of which are the frequency multiplier 228 output and one of the three accumulation timer 230 outputs, references 248, 250 and 252 which respectively are active or in an enabling state to AND 246 for periods of 2, 4 or 8 seconds. It is to be understood that the division chip 236 and accumulator timer outputs of the same time value are selected at any given time, i.e., either both of the 2 second, both of the 4 second, or both of the 8 second outputs are selected. Such corresponding selection of the accumulators and of the accumulator period timer outputs can be provided by any of a variety of well known switching means, including a ganged contact such as that of switch 254. Also included in accumulation period timer 230 is a clear and strobe section shown generally as 256. Briefly, the clear-strobe output 258 strobes the contents of the accumulator into the digit display 234 registers 244 following each accumulation period and the clear-strobe output 260 clears the digit display 234 registers 244 and the accumulator 232, it being understood that such strobing and clearing occur during selected phases of a count cycle so that they neither overlap each other nor overlap a phase designated for setting the accumulator.

In operation, the actual heart beat count is counted at a multiple of 60 for the selected period, and the count during that period is effectively divided by the divisor chip 236, the chip only updating accumulator counter register 244 once each series of consecutive counts equal to the accumulation period. The pulse rate count from the register 244 is strobed to display logic (not shown) at the end of each period. The other meter sections each employ a D'arsonval edgewise pointer indicator shown as 102, 116, and 158, although it is to be understood that these meters could also be digital readout meters.

The components for constructing the preferred embodiment illustrated in FIG. 3 are set forth in Table 2 below:

TABLE 2

Probe
R200 100 × 10³ ohms
R201 3.9 × 10³ ohms
R202 5.6 × 10³ ohms
R203 5.6 × 10³ ohms R204 4.7 × 10³ ohms R205 100 × 10³ ohms

Probe Drive 182
R270 11 × 10³ ohms
R271 1.5 × 10³ ohms
R272 3.0 × 10³ ohms
R273 12 × 10³ ohms
R274 10 × 10³ ohms
R275 3 × 10³ ohms
R276 24 × 10³ ohms
R277 10 × 10³ ohms
R278 1 × 10³ ohms
R279 10 × 10³ ohms
R280 110 ohms

Devices 16
200
R224 390 × 10³ ohms
R225 8.2 × 10³ ohms
R226 39 × 10³ ohms
R227 7.5 × 10³ ohms
R228 8.2 × 10³ ohms
R229 7.5 × 10³ ohms R230 82 × 10³ ohms
R254 10 × 10³ ohms
R231 10 × 10³ ohms
R232 10 × 10³ ohms
R233 10 × 10³ ohms
R234 10 × 10³ ohms
R235 10 × 10³ ohms
R236 10 × 10³ ohms
R236 3.9 × 10³ ohms

Meter 50
R238 100 × 10³ ohms
R239 100 × 10³ ohms

Meter 48
R240 100 × 10³ ohms

Meter 54
R241 2.5 × 10³ ohms
R242 2.5 × 10³ ohms
R243 2.5 × 10³ ohms
R244)
   ) 5 × 10³ ohms, 10 turn
R245)
   ) precision trimpots
R246)
R247 50 × 10³ ohms
R248 50 × 10³ ohms
R249 50 × 10³ ohms
R216 47 × 10³ ohms
R251 250 × 10³ ohms
R252 100 × 10³ ohms
R253 100 × 10³ ohms
R152 100 × 10³ ohms

Meter 52
R254 10 × 10³ ohms
R255 150 × 10³ ohms
R256 10 × 10³ ohms
R257 1 × 10⁶ ohms R258 2 × 10³ ohms R259 2 × 10³ ohms
R260 560 ohms
R261 5.1 × 10³ ohms 20 light emitting diode, Monsanto, MEGO
C200 56 microfarads
C201 68 microfarads, polarized, 6 volts w.v.d.c.
189 10 picofarads
C202
C203 0.01
*C204 2.2
188 JEDEC, 741, operational amplifier
24 Phototransistor, Fairchild FPF130

C220 0.1 microfarads
C221 120 picofarads
Q200, Q201 NPN, transistor, 2N2222A
Q202 NPN, transistor, 2N2907A
184 multivibrator, NE555V 60 = 1.0 microfarads
C208 = 1.0 microfarads
C209 = 100 microfarads, polarized, 16 volts w.v.d.c.
C210 = 50 microfarads, polarized, 16 volts, w.v.d.c.
C211 = .1 microfarads
C212 = 94 microfarads, polarized, formed by a pair of 47 microfarads, 20 w.v.d.c. capacitor connected in parallel A201)
    )
2)
    ) operational amplifier,
3)
    ) JEDEC 741
4)
    )
5)
D205) diode, 1N4148
    )
206) diode, 1N4148

SW 200 = pushbutton switch
116 = 0–200 micro. amp., edgewise, D'arsonval movement meter; Honeywell MCE 1

156 = 450 microfarads
C213 = .1 microfarad
A206 = operational amplifier JEDEC 741
SW 201 = pushbutton 227, Zener diode, 1N751A
D207) 1N4148, diode
D208) 1N4148, diode
D209 Zener diode, 1N751A
D210 Zener diode, 1N751A
226 Operational amplifier, JEDEC 741

IC 201 N and Gate, JEDEC 7404
IC 202 toggle flip-flop, JEDEC 74107

TABLE 2-continued

| | |
|---|---|
| R262 10 × $10^3$ ohms | IC 203 multivibrator, NE565 |
| R263 100 × $10^3$ ohms | IC 204 Inverter, N and Gate, 7404 |
| R264 1 × $10^3$ ohms | IC 205 Divide by ten chip, 7490 |
| R265 1 × $10^3$ ohms | IC 206 divide by twelve; 7492 |
| R266 2 × $10^3$ ohms | IC 207 N and Gate, 7413 |
| R267 2.2 × $10^3$ ohms | IC 208 Divide by six; 7492 |
| | IC 209 Divide by ten; 7490 |
| | IC 210 Counter; 7493 |
| | IC 211, IC 212, IC 213, IC 214 - Inverter, N and Gate, 7404 |
| | 246; IC 215, IC 216, IC 217 - N and Gate, 7411 |
| | IC 220, IC 221 - Counter, DM85L52 |
| | IC 222 N and Gate, 7404 |
| | IC 223 Inverter, N and Gate, 7404 |
| | IC 224 JK Flip-Flop, 74107 |
| | C214 = 2.2 microfarad, polarized, 25 volts, w.v.d.c. |
| | 215 = 0.01 microfarad |
| | 216 = 0.047 microfarad |
| | SW202 Three position, gauged contact |

Figure 6:
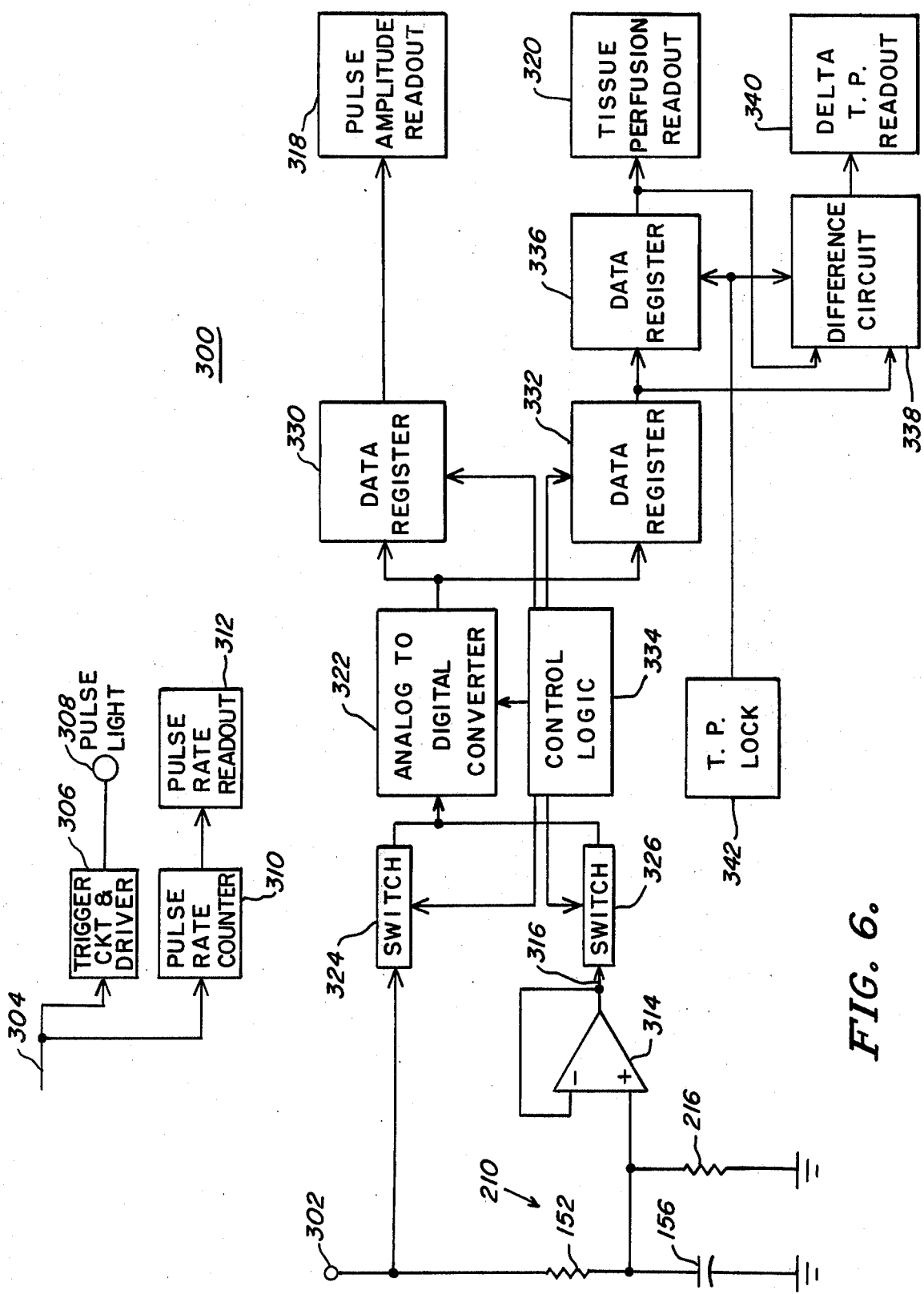

The exact form of readout for the four meter sections pulse amplitude 48, pulse wave 50, pulse rate 52, and tissue perfusion 54 is not considered critical to the present invention and may be any of a variety of well known forms, including but not limited to the aforedescribed pointer indicator meters. As one example of another form of readout, reference is made to FIG. 6 wherein a block diagram of a digital readout is shown. Also shown in FIG. 6 is so much of the meter section circuitry as must be modified for the digital form of readout. The inputs to the digital readout, shown generally as 300, are a node 302 and lead 304 which correspond to like numbered nodes and leads in the circuitry of FIG. 5, Part C.

Connected to lead 304 is a trigger circuit and driver 306, which is connected to a pulse light 308. Circuit 306 operates to flash pulse light 308 upon the occurrence of each heart beat pulse on lead 304. A pulse rate counter 310 is also connected to lead 304. Pulse rate counter 310 comprises an electronic digital counter circuit which functions to count the number of pulse waves occurring on lead 304 in a given period of time and to cause then to be displayed on pulse rate readout 312 which is a two-digit digital display for ease of reading by the medical personnel using the correlator. Appropriate circuits for use in counter 310 and readout 312 are well known in the art, and their exact configuration is not part of the present invention. In the preferred embodiment, counter 310 counts over a period of 12 seconds, and multiplies by five to give the effective pulse rate per minute.

Node 302 couples the pulse amplitude signal from the circuitry of FIG. 5, Part C, to a modified version of the tissue perfusion meter section 54. For the present digital readout 300, all that is required of the prior tissue perfusion meter section 54 is the integrater 210, which essentially comprises resistor 152, capacitor 156, and resistor 216. A unity gain operational amplifier 314 provides a high impedance between integrator 210 and the balance of the readout circuitry. Node 302 connects through resistor 152 to the non-inverting input of amplifier 314. Capacitor 156 and resistor 216 are connected in parallel between the non-inverting input of amplifier 314 and ground. The output of amplifier 314 at lead 316 is tied to the inverting input of the amplifier. Capacitor 156 performs an averaging or integrating function on the pulse amplitude signal. The resistor 156 provides a charging time constant, and the resistor 216 provides a different discharge time constant. Thus, the integrator 210 provides as its output a voltage which is equal to the averaged pulse amplitude. This voltage, as previously explained, is a quantitative measure of tissue perfusion.

As previously illustrated, both the pulse amplitude signal and node 302 and the tissue perfusion, or vaso bed, signal at 316 can be displayed by a pair of small ammeters, with appropriate scale factors. In the preferred embodiment, however, digital readouts are used and are shown as pulse amplitude readout 318 and the tissue perfusion readout 320. These readouts may be any of the readily available digital displays, such as segmented displays using light emitting diodes or gas discharge devices.

An analog to digital converter 322 is used to convert a pulse amplitude signal and the tissue perfusion signal to digital form for display by their respective readouts. In the preferred embodiment, a multiplexing arrangement is used so that only one analog to digital converter is required; of course if desired, a separate analog to digital converter could be used for each. In the preferred embodiment as shown in FIG. 6, a pair of switches 324 and 326 connect the pulse amplitude signal and tissue perfusion signals respectively to the input of converter 322. The two switches operate under the control of control logic which is designated by reference numeral 334. The output of analog to digital converter 322 is coupled to the inputs of data registers 330 and 332. The loading of data registers 330 and 332 is controlled by control logic 334. Digital data stored in register 330 is conveyed to the pulse amplitude readout 318. Similarly, digital data stored in register 332 is conveyed to another data register 336; the data from this register is conveyed to the tissue perfusion readout 320. The data outputs from data registers 332, 336, respectively are applied to the inputs of a difference circuit 338. The output of the difference circuit is applied to the delta tissue perfusion readout 340. The operation of difference circuit 338 and the loading of data register 336 are controlled by tissue perfusion lock circuit 342.

In operation, control logic 334 supervises the alternate conversions of the pulse amplitude and vaso bed signals. When a pulse amplitude conversion is made, control logic 334 energizes switch 324, thus applying the pulse amplitude signal to the analog to digital converter 322. Control logic 334 then enables converter 322 which then converts the analog pulse amplitude signal from node 302 to a digital value. At the end of the conversion, control logic 334 enables data register 330 so that the pulse amplitude signal in digital form is loaded into register 330. The contents of register 330, except when being updated, are continuously provided to and displayed by readout 318. When a tissue perfusion conversion is to be made, control logic 334 activates switch 326 to pass the analog tissue perfusion representation to converter 322. When the conversion is made, the control logic 334 loads the digital data into data register 332. In normal operation, this digital data is also applied to data register 336, and thence to the tissue perfusion readout 320.

When the tissue perfusion lock 342 is engaged, by means of a push button on the control panel, data register 336 is inhibited from accepting further data from data register 332. Accordingly, the last tissue perfusion data received is held in register 336 and displayed in readout 320 so long as the tissue perfusion lock is engaged. In this mode of operation, difference circuit 338 is enabled. Difference circuit 338 receives the locked or reference tissue perfusion reading from data register 336, and the present tissue perfusion reading from data register 332, which reading is continually being updated. Difference circuit 338 operates to calculate the difference between the two tissue perfusion readings, either plus or minus, and to display the difference in the delta tissue perfusion readout 340. The specific digital techniques used to perform the difference circuit function of element 338 are known in the art and do not form a part of the present invention. For example, a digital comparator could be used in conjunction with a presettable up-down counter. Depending upon whether the new tissue perfusion reading was higher or lower, the counter would be stepped up or down, with the number of steps required to make the two readings agree equaling the difference. The control logic for the digital readouts can be designed to give updated readings at convenient intervals, for example every few seconds.

I claim:

1. An apparatus for the non-invasive measurement of physiological data obtainable from monitoring blood flow in the circulatory ststem comprising:
   a. a pulsating light source adapted to be placed in non-invasive adjacent relationship to at least a portion of said circulatory system;
   b. light receiving means for receiving light signals from said light source after reflection from said circulatory system, and for generating electrical signals representative of said received light signals;
   c. a demodulating circuit means, connected to said light receiving means, for demodulating said electrical signals to amplitude modulate said pulsating light representations, and having an output terminal for transmitting said demodulating signals;
   d. circuit means, connected to said output terminal, for providing at least one of the electrical functions:
      i. averaging over a predetermined time interval,
      ii. detecting peak signal magnitudes, and
      iii. passing signals over a predetermined frequency band; and
   e. display means, connected to said circuit means, for providing a visual display of said electrical functions.

2. The apparatus of claim 1, further comprising a common housing wherein said pulsating light source and said light receiving means are mounted.

3. The apparatus of claim 2 wherein said pulsating light source further comprises a plurality of light emitting elements mounted in a symmetrical relationship about said light receiving means in said housing.

4. The apparatus of claim 3 wherein said pulsating light source further comprises three light-emitting diodes and said light receiving means further comprises a photocell.

5. The apparatus of claim 2 wherein said circuit means providing the electrical function of averaging over a predetermined time further comprises an integrating circuit means having the capability of averaging over at least 50 seconds.

6. The apparatus of claim 2 wherein said circuit means for providing the electrical function of passing signals over a predetermined frequency band further comprises a band pass filter circuit means for passing signals in the frequency range 3.75 – 6.75 Hz.

7. The apparatus of claim 2 wherein said circuit means for providing the electrical function of detecting peak signal magnitude further comprises a trigger circuit adjustable for detecting signal magnitudes representative of heart beats.

8. The apparatus of claim 2 further comprising a pulse amplitude circuit, connected to said output terminal, said pulse amplitude circuit having an integrating means for storing a voltage representative of said demodulated signals peak amplitudes; and display means for providing a visual display of the value of said stored voltage.

9. The apparatus of claim 8, further comprising a means for selectively discharging said integrating means, said discharging means comprising a timing circuit activated by said circuit means for detecting peak signal magnitude.

10. The apparatus of claim 9 wherein said timing circuit activation interval is predetermined and fixed.

11. The apparatus of claim 10 wherein said integrating means is discharged by said discharging means at a rate corresponding to the heartbeat rate.

12. An apparatus for the non-invasive measurement of physiological data obtainable from monitoring blood flow in the circulatory system, comprising:
   a. a housing including a pulsating light source adapted to be placed in non-invasive relationship and adjacent to at least a portion of the circulatory system;
   b. a light receiving means, located in said housing in fixed relationship to said pulsating light source, for receiving light signals reflected from said circulatory system portion, and for generating electrical signals representative of said received light signals;
   c. demodulating circuit means, connected to said light receiving means, for developing an envelope signal tracking said electrical signals' peak amplitudes;
   d. an averaging circuit connected to said demodulating circuit means, said averaging circuit having means for developing a voltage representative of said envelope signal average value over a time period of at least about 50 seconds; and
   e. an indicator connected to said averaging circuit, said indicator having a visual display means for displaying said average voltage signal.

13. The apparatus of claim 12 wherein said pulsating light source further comprises a plurality of light emitting elements mounted in a symmetrical relationship about said light receiving means in said housing.

14. The apparatus of claim 13 wherein said pulsating light source further comprises three light-emitting diodes and said light receiving means further comprises a photocell.

15. The apparatus of claim 14 wherein said pulsating light source frequency of pulsation is about 1000 Hz.

16. The apparatus of claim 15 wherein said pulsating light source has a duty cycle of about 10%, and a light wavelength of about 9000 A.

17. The apparatus of claim 16 wherein said averaging circuit further comprises an integrating capacitor circuit having a discharge time constant of about 50 seconds and a charge time constant of about 1 second.

18. The apparatus of claim 17 wherein said indicator further comprises a voltage meter of the D'Arsonval type.

19. An apparatus for the non-invasive measurement of physiological data obtainable from monitoring blood flow in the circulatory system, comprising:
   a. a housing including a pulsating light source adapted to be placed in non-invasive relationship and adjacent to at least a portion of the circulatory system;
   b. a light receiving means, located in said housing in fixed relationship to said pulsating light source, for receiving light signals reflected from said circulatory system portion, and for generating electrical signals representative of said received light signals;
   c. demodulating circuit means, connected to said light receiving means, for developing an envelope signal tracking said electrical signals' peak amplitudes;
   d. a band pass circuit connected to said demodulating circuit means, said band pass circuit having means for passing signals in the frequency range 3.75 – 6.75 Hz; and
   e. an indicator connected to said band pass circuit, said indicator having a visual display means for displaying signals passed.

20. The apparatus of claim 19 wherein said pulsating light source further comprises a plurality of light emitting elements mounted in a symmetrical relationship about said light receiving means in said housing.

21. The apparatus of claim 20 wherein said pulsating light source further comprises three light-emitting diodes and said light receiving means further comprises a photocell.

22. The apparatus of claim 21 wherein said pulsating light source frequency of pulsation is about 1000 Hz.

23. The apparatus of claim 22 wherein said pulsating light source has a duty cycle of about 10%, and a light wavelength of about 9000 A.

24. An apparatus for the non-invasive measurement of physiological data obtainable from monitoring blood flow in the circulatory system, comprising:
   a. a housing including a pulsating light source adapted to be placed in non-invasive relationship and adjacent to at least a portion of the circulatory system;
   b. a light receiving means, located in fixed relationship to said pulsating light source, for receiving light signals reflected from said circulatory system portion, and for generating electrical signals representative of said received light signals;
   c. demodulating circuit means, connected to said light receiving means for developing an envelope signal tracking said electrical signals' peak amplitudes;
   d. an amplitude indicating circuit connected to said demodulating circuit means, said amplitude indicating circuit having means for developing a voltage representative of the average value of said envelope signals' peak amplitudes;
   e. an indicator connected to said amplitude indicating circuit, said indicator having a visual display means for displaying said developed voltage signal.

25. The apparatus of claim 24 further comprising a peak detector circuit connected to said demodulating circuit means and to said amplitude indicating circuit, said peak detector circuit having means for detecting peak envelope signal voltages and for disabling said amplitude indicating circuit for a predetermined time interval after each peak voltage detection.

26. The apparatus of claim 25 wherein said pulsating light source further comprises a plurality of light emitting elements mounted in a symmetrical relationship about said light receiving means in said housing.

27. The apparatus of claim 26 wherein said pulsating light source further comprises three light-emitting diodes and said light receiving means further comprises a photocell.

28. The apparatus of claim 27 wherein said pulsating light source frequency of pulsation is about 1000 Hz.

29. The apparatus of claim 28 wherein said pulsating light source has a duty cycle of about 10%, and a light wavelength of about 9000 A.

* * * * *